(12) United States Patent
Lentz

(10) Patent No.: US 11,028,920 B2
(45) Date of Patent: Jun. 8, 2021

(54) PISTON FOR ELECTROMAGNETICALLY ACTUATE ABLE HYDRAULIC VALVE AND HYDRAULIC SYSTEM WITH THE ELECTROMAGNETICALLY ACTUATE ABLE HYDRAULIC VALVE AND A SIGNAL ELEMENT

(71) Applicant: ECO Holding 1 GmbH, Marktheidenfeld (DE)

(72) Inventor: Chris Lentz, Lake Orion, MI (US)

(73) Assignee: ECO Holding 1 GmbH, Marktheidenfeld (DE)

(*) Notice: Subject to any disclaimer, the term of this patent is extended or adjusted under 35 U.S.C. 154(b) by 36 days.

(21) Appl. No.: 16/045,612

(22) Filed: Jul. 25, 2018

(65) Prior Publication Data

US 2019/0032775 A1 Jan. 31, 2019

Related U.S. Application Data

(60) Provisional application No. 62/537,548, filed on Jul. 27, 2017.

(51) Int. Cl.
*F16H 61/02* (2006.01)
*G05D 16/20* (2006.01)
(Continued)

(52) U.S. Cl.
CPC .......... *F16H 61/0276* (2013.01); *F16K 11/07* (2013.01); *F16K 31/42* (2013.01);
(Continued)

(58) Field of Classification Search
CPC ................. F16H 61/0276; F16H 61/30; F16H 2061/0253; F16H 57/0006; F16K 47/00;
(Continued)

(56) References Cited

U.S. PATENT DOCUMENTS

| 2,698,632 | A | * | 1/1955 | Margrave | ................ F16K 11/07 137/599.08 |
| 3,513,877 | A | * | 5/1970 | Tennis | ................ F15B 13/0402 137/596.13 |
| 4,281,676 | A | * | 8/1981 | Morris | .................... F16D 25/14 137/102 |
| 4,469,011 | A | | 9/1984 | Loffler | |

(Continued)

FOREIGN PATENT DOCUMENTS

| DE | 102015215830 A1 | 2/2017 |
| EP | 1580469 A1 | 9/2005 |

(Continued)

*Primary Examiner* — Jessica Cahill
*Assistant Examiner* — Patrick C Williams
(74) *Attorney, Agent, or Firm* — Von Rohrscheidt Patents

(57) ABSTRACT

A piston for an electromagnetically actuatable hydraulic valve wherein the piston is configured cylindrical and axially movable along a central opening that extends along a longitudinal axis of a housing of the electromagnetically actuatable hydraulic valve, wherein plural connections of the housing are opened or closed according to a position of the piston wherein the plural connections are flow connected with the central opening, wherein the hydraulic valve is hydraulically actuatable by a signal element, wherein a damping system is provided for reducing oscillations of a signal pressure of the signal element that impacts the piston, and wherein the damping system is configured in the piston that includes a receiving cavity for receiving the damping system.

10 Claims, 4 Drawing Sheets

(51) Int. Cl.
    *F16K 11/07*      (2006.01)
    *F16K 31/42*      (2006.01)
    *F16K 47/00*      (2006.01)
    *F16H 57/00*      (2012.01)
    *F16H 61/30*      (2006.01)

(52) U.S. Cl.
    CPC ......... *F16K 47/00* (2013.01); *G05D 16/2013* (2013.01); *G05D 16/2024* (2019.01); *G05D 16/2097* (2019.01); *F16H 57/0006* (2013.01); *F16H 61/30* (2013.01); *F16H 2061/0253* (2013.01)

(58) Field of Classification Search
    CPC ..... F16K 31/42; F16K 11/07; G05D 16/2097; G05D 16/2024; G05D 16/2013
    See application file for complete search history.

(56) References Cited

U.S. PATENT DOCUMENTS

| | | | | |
|---|---|---|---|---|
| 4,478,237 | A | * | 10/1984 | Blake ..................... F16D 25/14 137/116.3 |
| 4,527,580 | A | * | 7/1985 | Chheda .................. F15B 1/103 137/1 |
| 5,934,323 | A | * | 8/1999 | Akimoto ................ F16J 15/025 137/625.69 |
| 7,104,273 | B1 | | 9/2006 | Stafford |
| 2004/0222579 | A1 | * | 11/2004 | Adoline ................ F16F 9/0218 267/250 |
| 2009/0250310 | A1 | | 10/2009 | Popp et al. |

FOREIGN PATENT DOCUMENTS

| | | |
|---|---|---|
| EP | 3073126 A1 | 1/2011 |
| WO | WO2011021730 | 2/2011 |

* cited by examiner

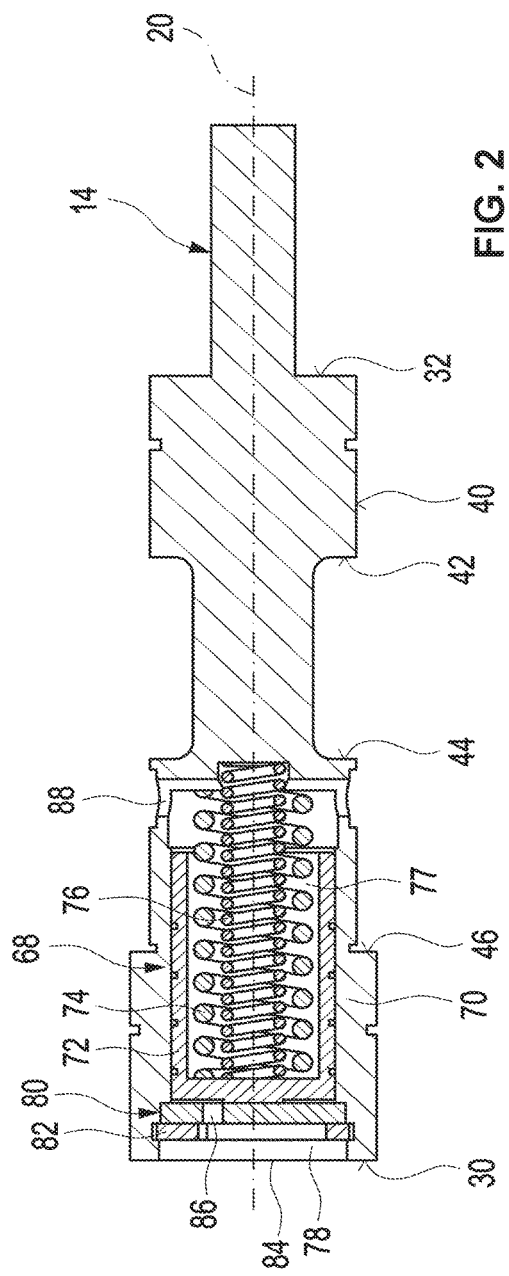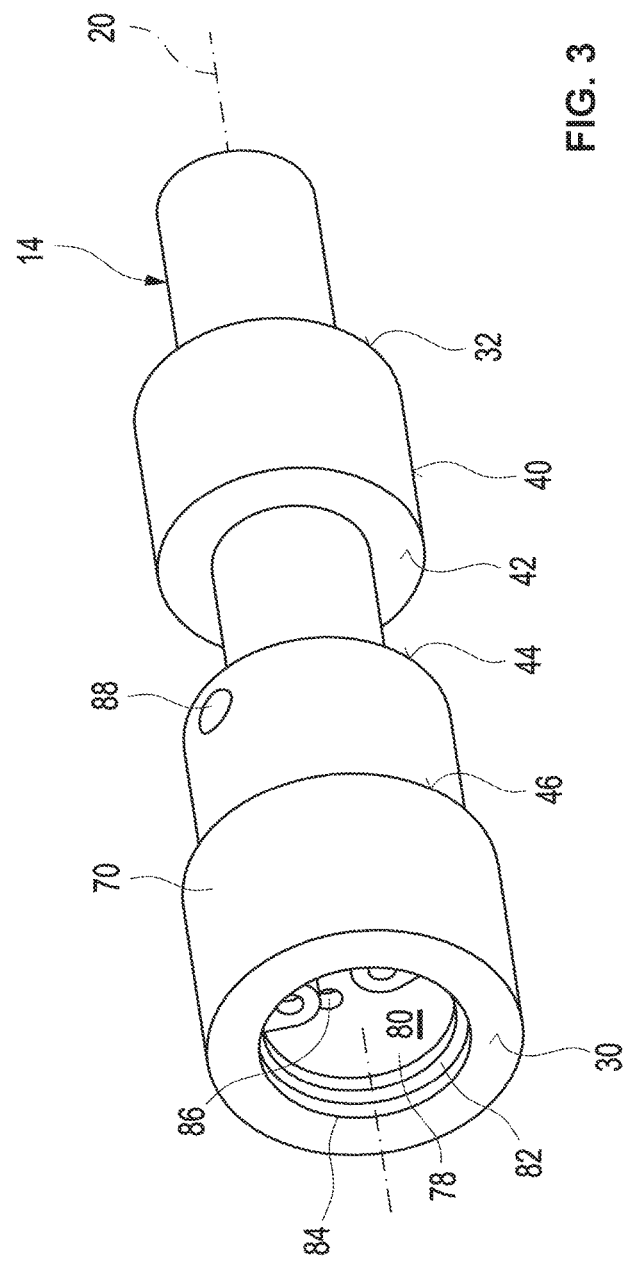

PISTON FOR ELECTROMAGNETICALLY ACTUATE ABLE HYDRAULIC VALVE AND HYDRAULIC SYSTEM WITH THE ELECTROMAGNETICALLY ACTUATE ABLE HYDRAULIC VALVE AND A SIGNAL ELEMENT

RELATED APPLICATIONS

This application is a non-provisional of U.S. provisional patent application 62/537,548 filed on Jul. 27, 2017 which is incorporated in its entirety by this reference.

FIELD OF THE INVENTION

The invention relates to a piston for an electromagnetically actuatable hydraulic valve and a hydraulic system with the electromagnetically actuatable hydraulic valve and a signal element.

BACKGROUND OF THE INVENTION

Advantageously current automatic transmissions, brake systems and clutches of motor vehicles use hydraulic valves, in particular electromagnetically actuatable hydraulic valves, wherein the hydraulic valve, also designated as pressure control valve, is loaded with a hydraulic pressure by an in particular electromagnetically configured signal element. The hydraulic valve includes a piston that is movably received in a housing and whose movement is initiated by a signal element. Thus, the piston that s movably received in the housing is moved due to the loading. As a function of a positioning of the piston a system pressure loading a consumer is obtained as an output pressure of the hydraulic valve. It is crucial that the system pressure is continuously stable thus a damping element or a damping system is typically provided on the pistons in order to eliminate or reduce interfering pressure oscillations.

U.S. Pat. No. 4,469,011 discloses a hydraulic valve configured as a pressure control valve wherein the hydraulic valve includes a damping element which is received in a second housing that is adjacent to a housing of the hydraulic valve. The damping element is received in a pressure control loop that is configured between a consumer and the hydraulic valve.

The publication document EP 1 580 469 A1 discloses a hydraulic pressure control valve which provides a chamber for damping the hydraulic fluid that loads the piston in the housing of the pressure control valve.

U.S. Pat. No. 7,104,273 B1 discloses a hydraulic valve whose piston is loaded by a coil spring of a damper wherein the damper includes a damping cylinder that is arranged between the signal element and the coil spring.

The publication document US 2009/0250310 A1 discloses a hydraulic valve for a transmission device wherein a damper is associated with a signal element wherein the damper is arranged in a pressure control loop between the hydraulic valve and the signal element.

The hydraulic valves that are known in the art include additional installation space for the damping element which can also be designated as a damping system. This is independent from the damping element being received in a housing of the hydraulic valve or in a housing that is detached from the hydraulic valve or a consumer housing. This means put differently that the known hydraulic valves have a large installation space requirement due to the damping elements or damping systems that have to be arranged. Thus, it is also typical in a multi-speed transmission to arrange the damping elements or damping systems which are to be associated with the corresponding control valves in a receiving housing that is adjacent to the housing of the hydraulic valve. This causes a very large installation space requirement in particular for more than six transmission gear stages.

BRIEF SUMMARY OF THE INVENTION

Thus, it is an object of the invention to provide a piston for a hydraulic valve, in particular for an electromagnetically actuatable hydraulic valve wherein the piston facilitates an installation space optimized configuration of the hydraulic valve. It is another object of the invention to provide a hydraulic system with an in particular electromagnetically actuatable hydraulic valve and a signal element.

The objects are achieved according to the invention by a piston for an in particular electro magnetically actuatable hydraulic valve with the features of patent claim 1. Another object of the invention is achieved by a hydraulic system with an electro magnetically actuate able hydraulic valve and a signal element with the features of patent claim 12. Advantageous embodiments with useful and nontrivial improvements of the invention can be derived from the respective dependent claims.

The invention relates to a piston for an in particular electro magnetically actuatable hydraulic valve wherein the piston is configured cylindrical and wherein the piston is axially movable along a central opening that extends along a longitudinal axis of a housing of the hydraulic valve. According to a positioning of the piston different connections of the housing are opened and closed which are flow connected with the central opening. The hydraulic valve is hydraulically actuatable by a signal element. In order to reduce oscillations of a signal pressure of the signal element impacting the piston a damping system is provided. According to the invention the damping system is configured in the piston wherein the piston includes a receiving cavity for receiving the damping system. It is an advantage of the invention to provide a compact piston which is configured with a damping system and which facilitates a compact and installation space optimized hydraulic valve which requires reduced installation space compared to the prior art. The damping system can include one component, but it can also be made from several components.

Thus, the instant invention provides a piston which receives a damping system in a simple manner so that additional installation space that is required to arrange the damping system can be omitted.

In one embodiment of the piston according to the invention the damping system is configured coaxial with the longitudinal axis. Since the piston is movably received along the longitudinal axis in the housing the coaxial arrangement of the damping system causes a damping of the hydraulic fluid loading the piston in its movement direction which achieves an effective damping of the damping system.

In another embodiment of the piston according to the invention the damping system includes a non-elastic element and/or an elastic element. The non-elastic element facilitates a separation of different pressure control loops. Thus, a first pressure control loop is the pressure control loop that is influenceable by the signal element and the second pressure control loop is the control loop that is influenced by the hydraulic valve and whose pressure impacts a consumer. The elastic element causes a damping of the pressure of the pressure control loop including the signal element in combination with the non-elastic element, put differently, a damping of the signal pressure impacting the piston. Thus, the configuration of the piston with the two elements leads to a combination of the two functions separation and damping while providing an installation space optimized configuration.

In order to provide further installation space optimization the non-elastic element is configured to receive the elastic element.

In another embodiment the piston includes an inlet opening of the receiving cavity at a face oriented towards the signal element wherein the damping system is insert able through the inlet opening. Simple assembly of the damping system in the piston is a first advantage of this embodiment. Another advantage is the possible direct loading of the damping system with the signal pressure. This means put differently that a portion of the signal pressure impacts the piston directly, this means on a piston element that is oriented towards the signal element which is configured annular due to the inlet opening and the other portion of the signal pressure impacts the piston through the elastic element which is configured in particular as a coil spring. Thus the damping system advantageously influences both portions of the signal pressure.

An arrangement of a closure element in the inlet opening that substantially closes the inlet opening has the advantage that the damping system has an axial safety against a displacement from the receiving opening, put differently against loss. Another advantage of the closure element that substantially closes the inlet opening is that a complete contact of the damping element at the closure element provides the option to close the receiving opening entirely relative to an entry of hydraulic fluid or hydraulic fluid can flow into the receiving opening in case the damping system does not contact the closure element so that an opening remains since the closure element does not completely close the inlet opening. Advantageously the opening is provided as a circular hole in the closure element. Thus, a typical connection opening that is to be formed according to the prior art in order to provide a flowable connection of the damping system with a signal cavity that is configured between the signal element and the piston wherein the signal pressure is provided in the signal cavity can thus be provided in a simple manner by the opening.

In order to arrange a safety element in particular in the inlet opening so that the closure element is arranged between the safety element and the damping system is used for additionally axially secure the damping system in the piston against loss. By the same token it secures the closure element against loss.

The signal element can be configured to provide a hydraulic signal that impacts the piston wherein the signal element is advantageously configured in a form of an electromagnetic actuator since the electromagnetic actuator delivers a required signal in a short time period.

A second aspect of the invention relates to a hydraulic system with a particularly electro magnetically actuatable hydraulic valve and a signal element wherein the hydraulic valve includes a housing and a piston that is movably received in a central opening. The piston is hydraulically movable by the signal element, wherein flowable connections are configured in the housing which are flow connected with the central opening, wherein the piston is configured according to one of the claims 1-11.

According to the invention the signal element is at least partially received in a receiving opening of the housing. This means put differently that the hydraulic system includes the hydraulic valve as well as the signal element in a single housing. This provides a secure connection of the signal element with the hydraulic valve wherein in particular a short signal path is providable between the piston and the signal element wherein the short signal path facilitates improved response of the piston due to the short signal path which is possible in particular when the central opening and the receiving opening are coaxially arranged. Furthermore seals between the two components can be eliminated in a cost effective manner when the signal element and the hydraulic valve are received in a common housing.

Thus, an installation space optimized hydraulic system is provided which is characterized by secure damping of the hydraulic signal and thus by reliably providing an essentially constant pressure for the consumer.

BRIEF DESCRIPTION OF THE DRAWINGS

Additional advantages, features, and details of the invention can be derived from the subsequent description of advantageous embodiments or from the drawing figure. The features and feature combinations recited in the preceding description and the features and feature combinations subsequently recited in the figure description and/or in the figures by themselves are not only usable in the respectively recited combination but also in other combinations or by themselves without departing from the spirit and scope of the invention. Identical or functionally equivalent elements are associated with identical reference numerals. For reasons of clarity the elements may not be provided with reference numerals in all figures without losing their association, wherein:

FIG. 2 illustrates a longitudinal sectional view of a piston according to the invention, in particular for an electromagnetically actuatable hydraulic valve for the hydraulic system according to FIG. 1;

FIG. 3 illustrates a perspective view of the piston according to FIG. 2;

DETAILED DESCRIPTION OF THE INVENTION

Figure 1:
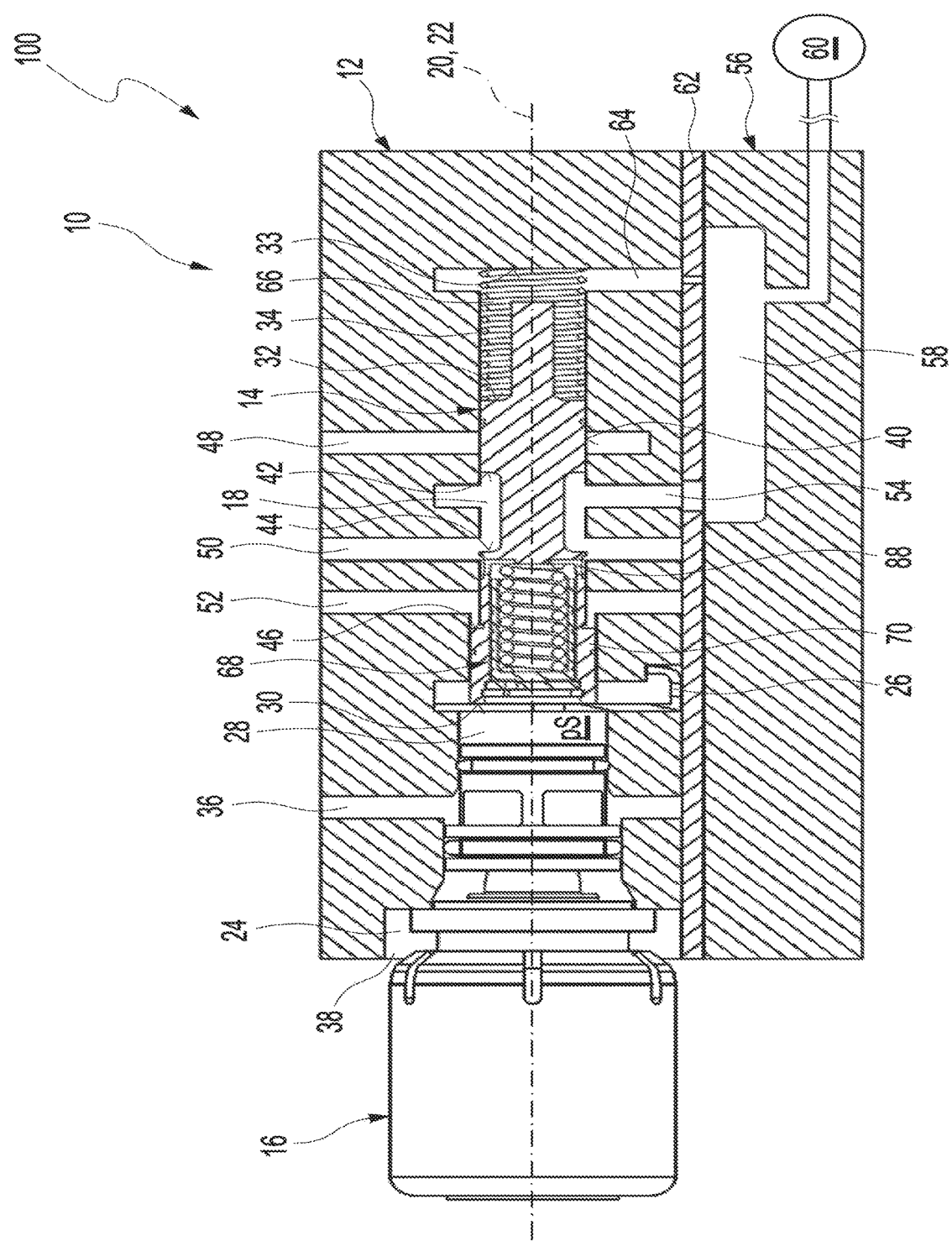
FIG. 1 illustrates a semi-sectional view of a hydraulic system according to the invention.

A hydraulic system 100 according to the invention with an electromagnetically actuatable hydraulic valve 10 is configured according to FIG. 1. The hydraulic system 100 includes a housing 12 which receives a piston 14 according to the invention and a signal element 16 at least partially. This means put differently that the housing 12 is a housing of the hydraulic valve 10 at least partially.

The piston 14 is arranged in a central opening 18 of the housing 12 which includes a longitudinal axis 20, wherein the signal element 16 with its element axis 22 is positioned coaxial with the central opening 18 in a receiving opening 24 of the housing 12. The signal element 16 is arranged non-moveable in the housing 12, whereas the piston 14 is configured axially moveable along the longitudinal axis 20. The piston 14 is configured cylindrical and hollow cylindrical in sections.

For an axial movement limitation of the piston 14 in a direction of the signal element 16 a limiting element 26 is received non-moveable in the housing 12 between the signal element 16 and the piston 14. The limiting element 26 is configured flowable so that a pressure loading of the piston 14 can be performed starting from the signal element 16.

A signal pressure cavity 28 is configured between the central opening 18 and the receiving opening 24 in the housing 12 wherein the signal pressure cavity is filled with hydraulic fluid having a signal pressure pS that is generated by the signal element 16. The signal pressure pS impacts a face 30 of the piston 14 that is oriented towards the signal element 16. The receiving opening 24 and the central opening 18 are sealed relative to the signal pressure cavity 28.

An annular surface 32 of the piston 14 that is oriented away from the face 30 is loaded with a loading force of a loading element 34 that is received between the annular surface 32 and an opening wall 33 of the central opening 18 that is arranged opposite to the annular surface 32. When the signal pressure pS is greater than the loading force of the loading element 34, the piston 14 is axially moved into a direction that is oriented away from the signal element 16. However, when the signal pressure pS is smaller than the loading force of the loading element 34 the piston 14 is moved by the loading element 34 in a direction towards the signal element 16 until the piston either contacts the limiting element 26 or stops thereon or until an equilibrium between the loading force and signal pressure pS is provided. The loading element 34 is configured as a coil spring.

In order to supply the hydraulic valve 10 with hydraulic fluid the housing 12 includes plural flowable connections 36, 38, 48, 50, 52, 54, 64, which are provided for hydraulically loading and unloading the piston 14 and the signal element 16.

Thus a flowable first supply connection 36 is configured to supply the signal element 16 with the hydraulic fluid. Through the first supply connection 36 the signal element 16 is loaded with the hydraulic fluid which causes the signal pressure ps. The hydraulic fluid flows from the receiving opening 24 through a first relief connection 38.

The connections 48, 50, 52, configured for loading the piston 14 with pressure and unloading it, this means for reducing the pressure impacting the piston 14, are flowable from the central opening 18 as a function of a position the piston 14.

Figure 4:
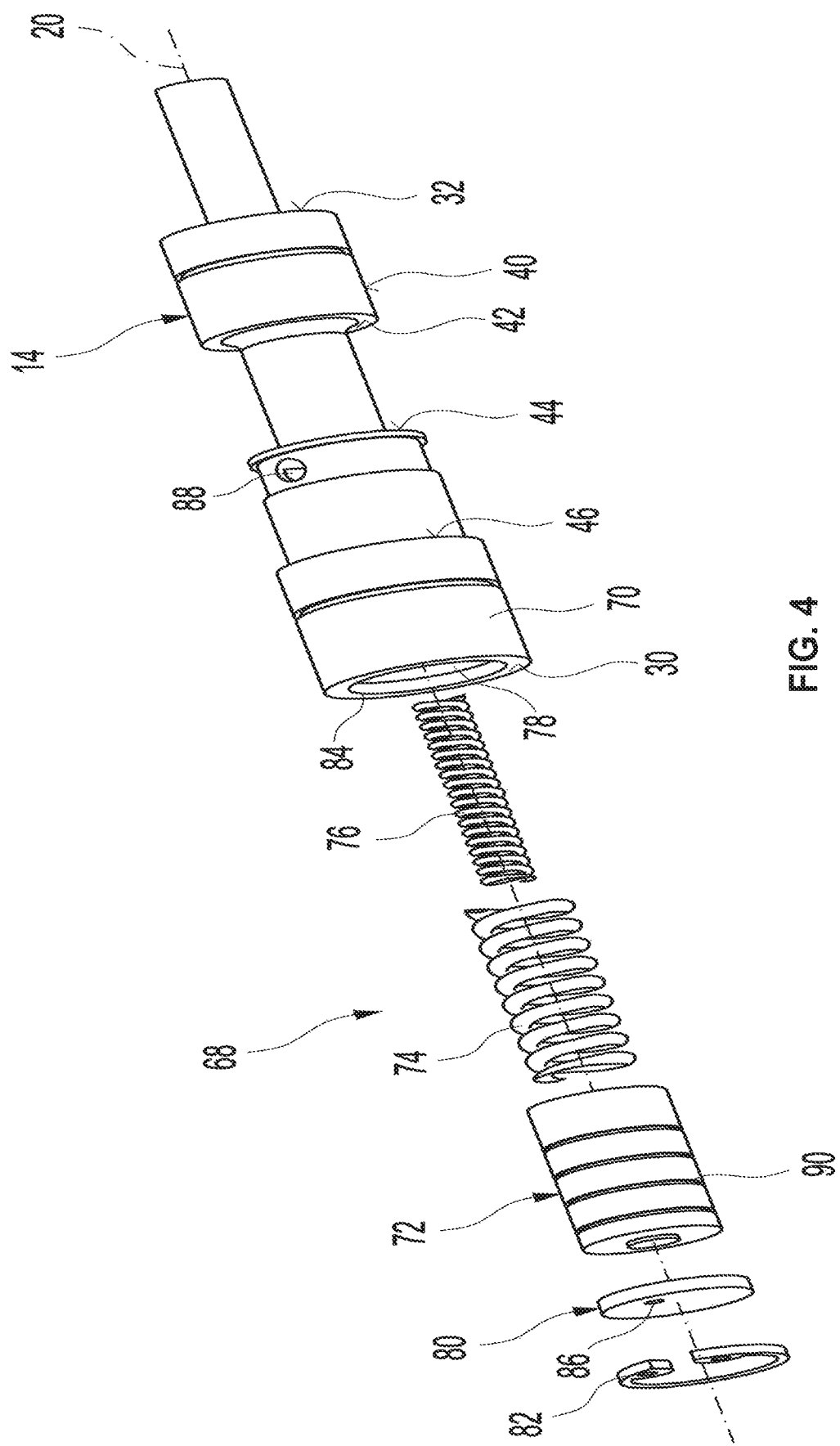
FIG. 4 illustrates an exploded view of the piston according to FIG. 2.

In order for the piston 14 to be positionable by the hydraulic fluid the piston 14 includes a first control surface 42 originating from its enveloping surface 40, a second control surface 44, and a third control surface 46, wherein the control surfaces 42, 44, 46 are configured annular as evident in particular from FIGS. 3 and 4. The first control surface 42 is associated with the second supply connection 48 of the housing 12, the second control surface 44 is associated with the second relief connection 50 of the housing 12 and the third control surface 46 is associated with the third supply connection 52 which is also usable as a relief connection.

A flowable consumer connection 54 is configured between the second supply connection 48 and the second relief connection 50 in the housing 12 and flow connected with a consumer 60 by a consumer connection 58 configured in an auxiliary housing 56. The consumer 60 can be for example a clutch, a brake or a transmission, however, the embodiments of the consumer 60 are not limited to these examples.

The housing 12 is permanently flow connected with the auxiliary housing 56 wherein a seal element 62 is arranged between the housing 12 and the auxiliary housing 56. The housing 12 can also be received in the auxiliary housing 56 and can be at least partially enveloped by the auxiliary housing 56.

The piston 14 is illustrated in FIG. 1 in a first position in which the consumer connection 54 is released, put differently opened, in order to be able to load the consumer 60. In this first position the piston 14 contacts the limiting element 26. The coil spring 34 is unloaded in this first position and imparts a spring pressure due to its spring force upon the annular surface 32 which presses the piston 14 against the limiting element 26. A hydraulic pressure that impacts the third control surface 46 supports the spring pressure wherein the hydraulic pressure can engage due to the opened third supply connection 52 at the third control surface 46. Since the second relief connection 50 is also released, put differently, opened, no pressure impacts the consumer 60.

In a non-illustrated additional position the hydraulic pressure in the signal pressure cavity causes a movement of the piston 14 in a direction of the coil spring 34 which is being compressed. As soon as the second supply connection 48 is released by the first control surface 42, the first control surface 42 can be loaded with a pressure due to an inflow of hydraulic fluid through the second supply connection 48 into the central opening 18 wherein the pressure supports the positioning. Furthermore, the consumer connection 54 is also released in this position, wherein, however, the pressure that is supplied in the second supply connection 48 is imparted upon the consumer 60 since the second relief connection 50 is closed by the piston 14 and can thus cause a pressure loading of the consumer 60.

Another relief connection 64 is provided in the housing 12 in a portion of the coil spring 34 wherein the relief connection is flow connected with the consumer connection 58. This additional relief connection 64, which flow connects an operating cavity 66 of the central opening 18 with the consumer connection 58 is used for improved, in particular, quicker movement of the piston 14, since a pressure compensation in the operating cavity 66 can be provided through the additional relief connection 64.

In order to prevent or at least reduce pressure variations in the signal pressure cavity 28 which impact an axial movement of the piston 14 and thus at least indirectly the adjustment or setting of the consumer 60, a damping system 68 is provided. The damping system 68 is arranged in the piston 14 in a hollow cylindrical section 70 of the piston 14, c.f., FIG. 2.

The damping system 68 includes as evident in particular from FIGS. 2 and 4, a first damping element 72 configured as a hollow non-elastic damping cylinder, an elastic second damping element 74, and an elastic third damping element 76. The second damping element 74 like the third damping element 76, is configured as a coil spring. However, the two elastic damping elements 74, 76 can also be configured in another suitable form. In order to provide improved damping two elastic elements 74, 76 are provided. Advantageously the two elastic elements can be provided as two coaxial coil springs 74, 76 that are wound in opposite directions as illustrated in FIGS. 2 and 4. By the same token, only one of the elastic damping elements 74, 76 can be provided.

The two elastic damping elements 74, 76 are received in the damping cylinder 72 in its element receiver cavity 77 in a reduced installation space. The damping system 68 is received in a receiving cavity 78 that is configured in the piston 14 and secured against loss by a flowable cover element 80, which is configured as a disk. The receiving cavity 78 includes an inlet opening 84 that is configured at the face 30. In order to secure the cover element 80 a safety element 82 configured as a clip ring is received in the receiving cavity 78, wherein the cover element 80 is arranged between the damping system 68 and the safety element 82.

The cover element 80 separates a first pressure control loop that is configured between the signal element 16 and the piston 14 and configured to adjust the signal pressure that impacts the piston 14 from a second control loop that is configured between the hydraulic valve 10 and the consumer 60. Both pressure control loops have hydraulically independent pressures which are adjusted or configured in the respective control loop. In order for hydraulic fluid from the first pressure control loop to flow to the damping system 68 an opening 86 is provided which is advantageously configured as a circular hole in the cover element 80. This opening 86 is closed when the damping system 68, in the illustrated embodiment the non-elastic first damping element 72 is positioned to contact the cover element 80 as illustrated in FIG. 1.

The piston 14 includes a pass-through opening 88 in a portion of the damping system 68 at a side of the piston 14 that is oriented away from the cover element 80 so that hydraulic fluid can flow in or out through the pass-through opening 88 into the hollow first damping element 72 according to a positioning of the piston 14 and of the first damping element 72.

The first damping element 72 includes circumferential grooves 90 at its outer circumference in order to improve its positioning, this means, put differently, to provide quicker movability.

Figure 5:
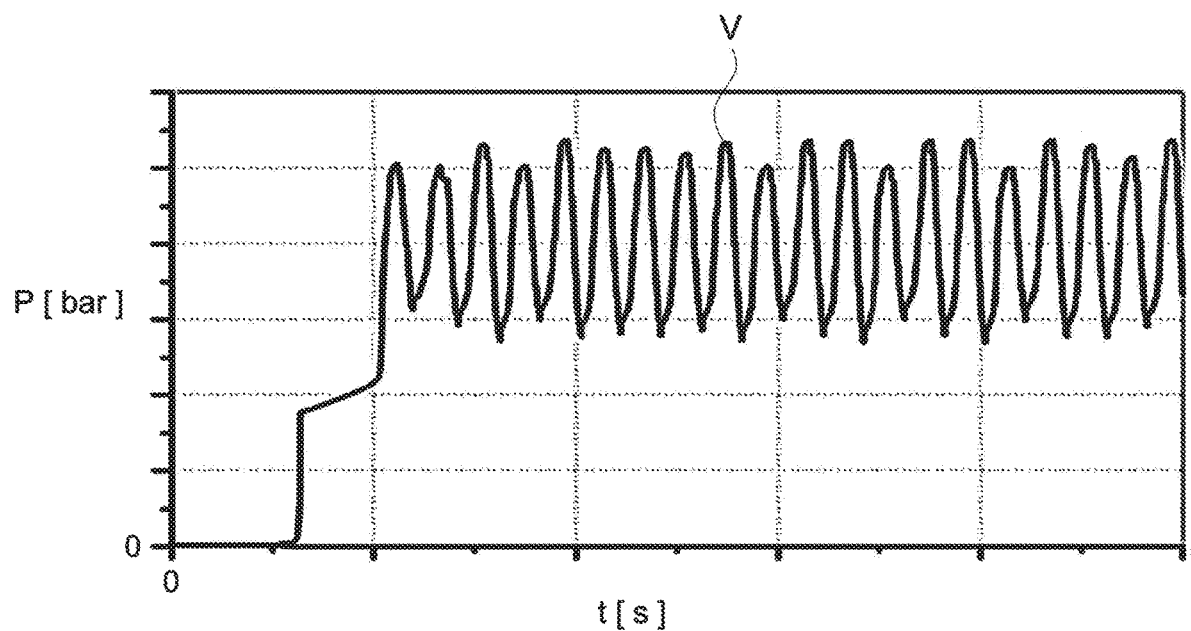
FIG. 5 illustrates a time-based pressure diagram of a pressure at a consumer that is generated by a prior art hydraulic valve.
Figure 6:
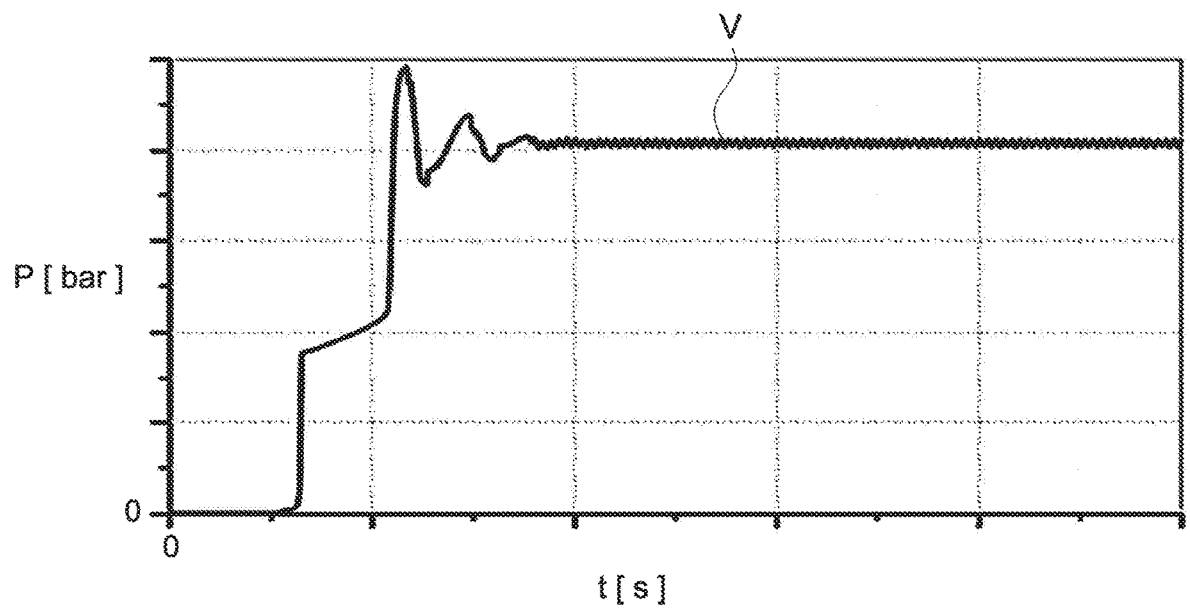
FIG. 6 illustrates a time-based pressure diagram of a pressure at the consumer that is generated by the hydraulic valve of the hydraulic system according to FIG. 1.

FIGS. 5 and 6 respectively illustrate pressure diagrams V over time which impact the consumer 60. The pressure diagram V which is illustrated in FIG. 5 was generated by a prior art hydraulic valve 10 and does not include a damping system 68.

The pressure diagram V illustrated in FIG. 6 represents a pressure that is generated by the hydraulic valve 10 according to the invention and impacts the consumer 60. It is evident that the consumer 60 is provided with a constant pressure after a short back and forth adjustment time.

REFERENCE NUMERALS AND DESIGNATIONS 10 hydraulic valve
12 housing
14 piston
16 signal element
18 central opening
20 longitudinal axis
22 element axis
24 receiving opening
26 limiting element
28 signal pressure cavity
30 face
32 annular surface
33 opening wall
34 loading element
36 first supply connection
38 first relief connection
40 enveloping surface
42 first control surface
44 second control surface
46 third control surface
48 second supply connection
50 second relief connection
52 third supply connection
54 consumer connection
56 accessory housing
58 consumer connection
60 consumer
62 seal element
64 relief connection
66 operating cavity
68 damping system
70 section
72 first damping element
74 second damping element
76 third damping element
78 receiving cavity
80 cover element
82 safety element
84 inlet opening
86 opening
88 pass through
90 circumferential groove
100 hydraulic system
pS signal pressure

What is claimed is:
1. An electromagnetically actuatable hydraulic valve, comprising:
a piston arranged in a housing; and
a damping system including a first hollow damping element that is axially movable in the piston and a spring element that is axially supported at the piston and at the first hollow damping element,
wherein the piston is configured cylindrical and axially movable along a central opening that extends along a longitudinal axis of the housing of the electromagnetically actuatable hydraulic valve,
wherein plural connections of the housing are opened or closed according to a position of the piston wherein the plural connections are flow connected with the central opening,
wherein the piston is axially movable by a force generated directly at the piston by a hydraulic signal pressure from a signal element,
wherein the damping system reduces oscillations of the force generated directly at the piston by the hydraulic signal pressure from the signal element when the piston is at the position,
wherein an entirety of the damping system including an entirety of the first hollow damping element and an entirety of the spring element is received in a receiving cavity configured in the piston,
wherein the entirety of the damping system always moves together with the piston when the piston moves,
wherein the first hollow damping element seals against the signal pressure along an axial travel range of the first hollow damping element in the piston, and
wherein the first hollow damping element partially envelops the spring element.
2. The electromagnetically actuatable hydraulic valve according to claim 1, wherein the damping system is configured coaxial with the longitudinal axis.

3. The electromagnetically actuatable hydraulic valve according to claim 1,
   wherein the piston includes an inlet opening of the receiving cavity at a face of the piston that is oriented towards the signal element, and
   wherein the damping system is insertable through the inlet opening.

4. The electromagnetically actuatable hydraulic valve according to claim 3, wherein a cover element with a circular opening is arranged in the inlet opening and closes the inlet opening outside of the circular opening.

5. The electromagnetically actuatable hydraulic valve according to claim 1, wherein the damping system is axially secured in the piston by a safety element.

6. The electromagnetically actuatable hydraulic valve according to claim 1, wherein the signal element is an electromagnetic actuator.

7. A hydraulic system, comprising:
   the electromagnetically actuatable hydraulic valve according to claim 1,
   wherein the signal element is at least partially received in a receiving opening of the housing.

8. The hydraulic system according to claim 7, wherein the housing includes additional connections that are flow connected with the receiving opening.

9. The hydraulic system according to claim 7, wherein the central opening is arranged coaxial with the receiving opening.

10. The electromagnetically actuatable hydraulic valve according to claim 1, wherein the spring element includes two coaxial coil springs that are wound in opposite directions.

* * * * *